(12) United States Patent
Culbertson et al.

(10) Patent No.: US 12,304,152 B2
(45) Date of Patent: May 20, 2025

(54) ULTRASOUND PROBE HANDLE

(71) Applicant: KONINKLIJKE PHILIPS N.V., Eindhoven (NL)

(72) Inventors: Timothy David Culbertson, Reedsville, PA (US); James Christopher Taylor, State College, PA (US); Alex Moore, Reedsville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 631 days.

(21) Appl. No.: 17/607,061

(22) PCT Filed: May 8, 2020

(86) PCT No.: PCT/EP2020/062914
§ 371 (c)(1),
(2) Date: Oct. 28, 2021

(87) PCT Pub. No.: WO2020/229358
PCT Pub. Date: Nov. 19, 2020

(65) Prior Publication Data
US 2022/0242053 A1 Aug. 4, 2022

Related U.S. Application Data

(60) Provisional application No. 62/846,929, filed on May 13, 2019.

(51) Int. Cl.
*B29C 65/08* (2006.01)
*A61B 8/00* (2006.01)
(Continued)

(52) U.S. Cl.
CPC ............ *B29C 65/08* (2013.01); *A61B 8/4444* (2013.01); *B29C 65/4835* (2013.01);
(Continued)

(58) Field of Classification Search
CPC .... A61B 8/4444; A61B 8/4455; A61B 8/4472
See application file for complete search history.

(56) References Cited

U.S. PATENT DOCUMENTS

| 4,207,660 A | 6/1980 | Rao et al. |
| 2015/0025176 A1 | 1/2015 | Eagle et al. |

(Continued)

FOREIGN PATENT DOCUMENTS

| CN | 203353004 U | * 12/2013 |
| JP | 2000135740 A | 5/2000 |

(Continued)

OTHER PUBLICATIONS

International Search Report and Written Opinion of PCT/EP2020/062914 mailed Aug. 25, 2020.

*Primary Examiner* — Livius R. Cazan

(57) ABSTRACT

System, devices, and methods for coupling portions of a medical device handle are provided. A male portion (202) and a female portion (204) of the handle may be coupled together using a sealant (244) such as room temperature vulcanized silicone rubber (RTV) using in conjunction with ultrasonic welding. The RTV may be applied to one of the male or female portions and the portions may be joined using a tongue (215) and groove (2259 connection, displacing the RTV from the weld site. The RTV helps to seal the bondline (206) after ultrasonic welding.

6 Claims, 20 Drawing Sheets

(51) Int. Cl.
    *B29C 65/48*         (2006.01)
    *B29C 65/72*         (2006.01)
    *B29L 31/00*         (2006.01)
    *B29L 31/46*         (2006.01)

(52) U.S. Cl.
    CPC ......... *B29C 65/72* (2013.01); *B29L 2031/463* (2013.01); *B29L 2031/753* (2013.01)

(56) References Cited

U.S. PATENT DOCUMENTS

2015/0148680 A1* 5/2015 Hirayama ............ A61B 8/4444
                                                                         600/459
2018/0317883 A1   11/2018 Huhtamaki et al.

FOREIGN PATENT DOCUMENTS

| JP | 2009181830 A | * | 8/2009 |
|---|---|---|---|
| JP | 2014137909 A | | 7/2014 |
| KR | 100632151 B1 | | 10/2006 |

\* cited by examiner

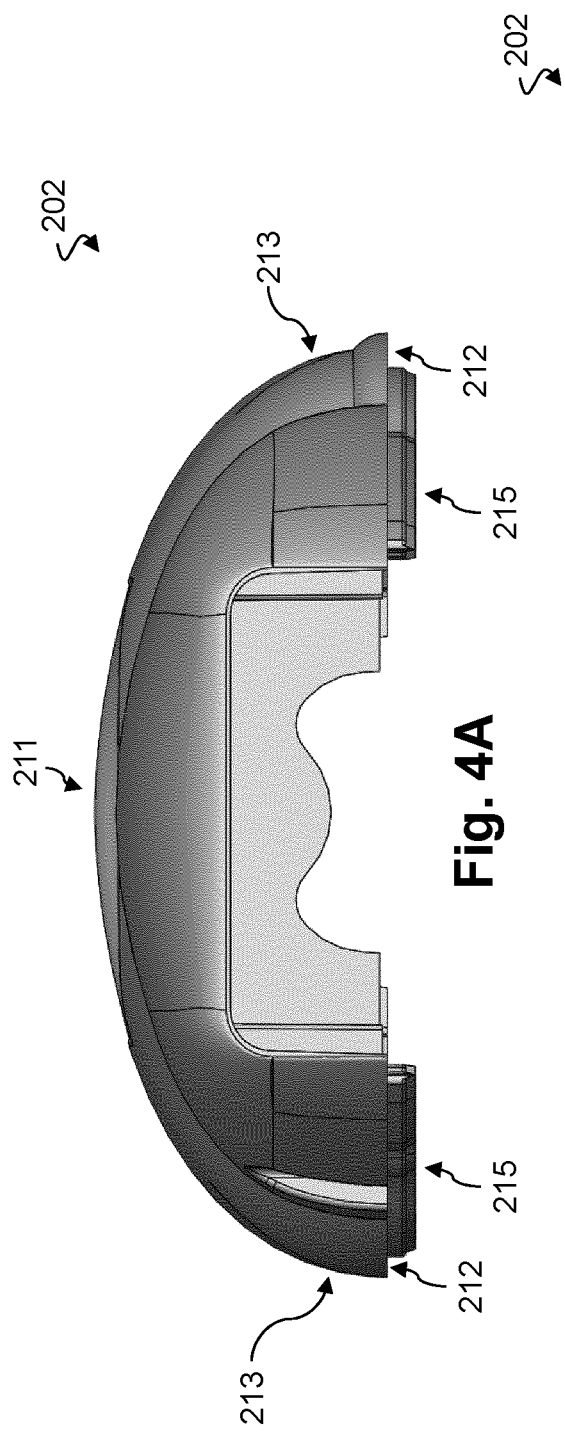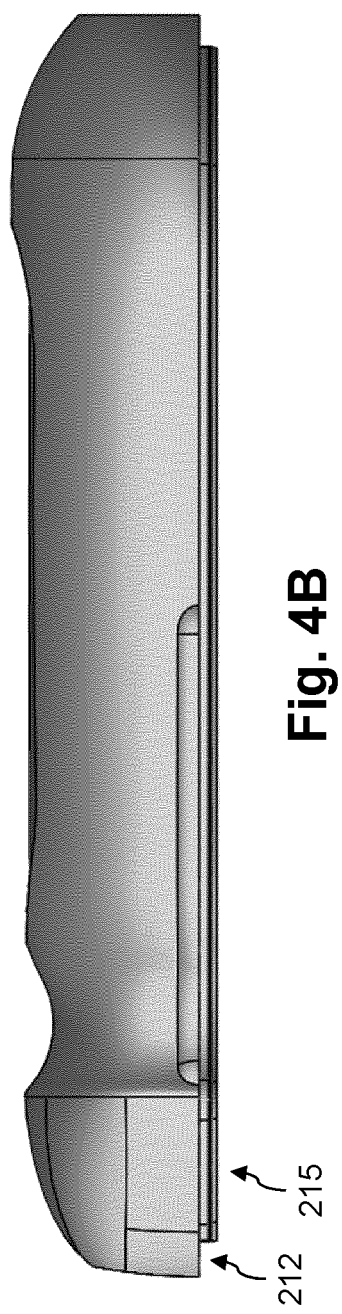
Fig. 4A
Fig. 4B

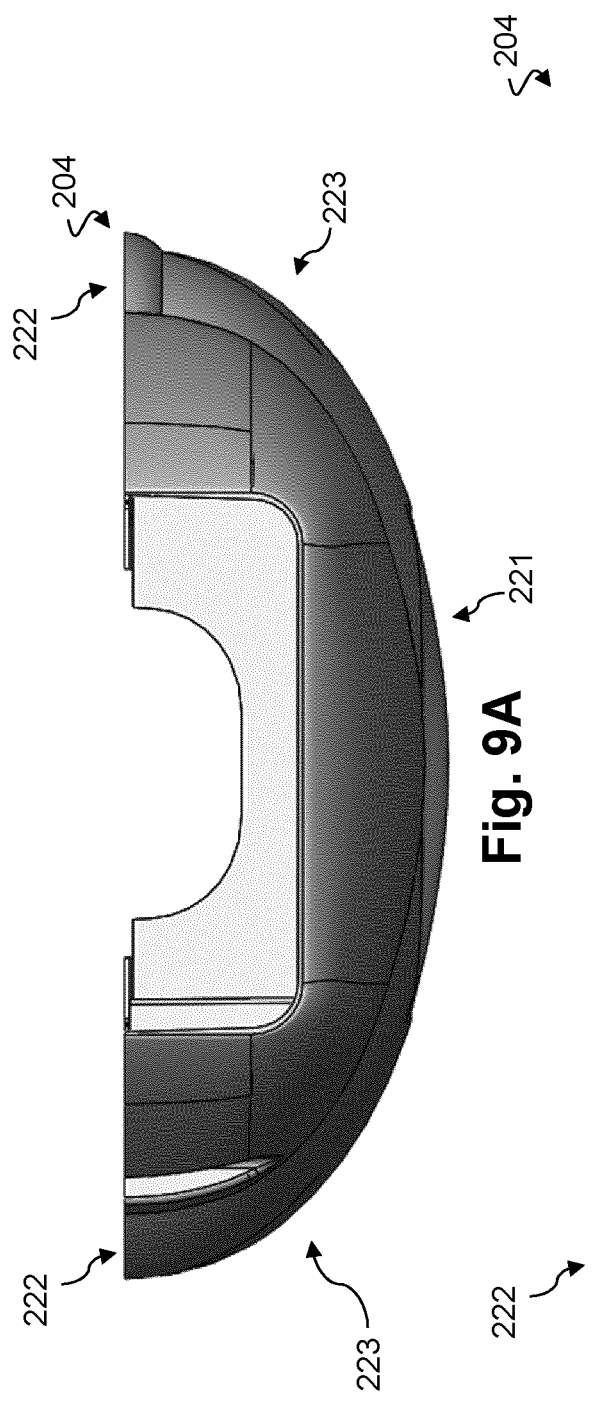
Fig. 9A
Fig. 9B

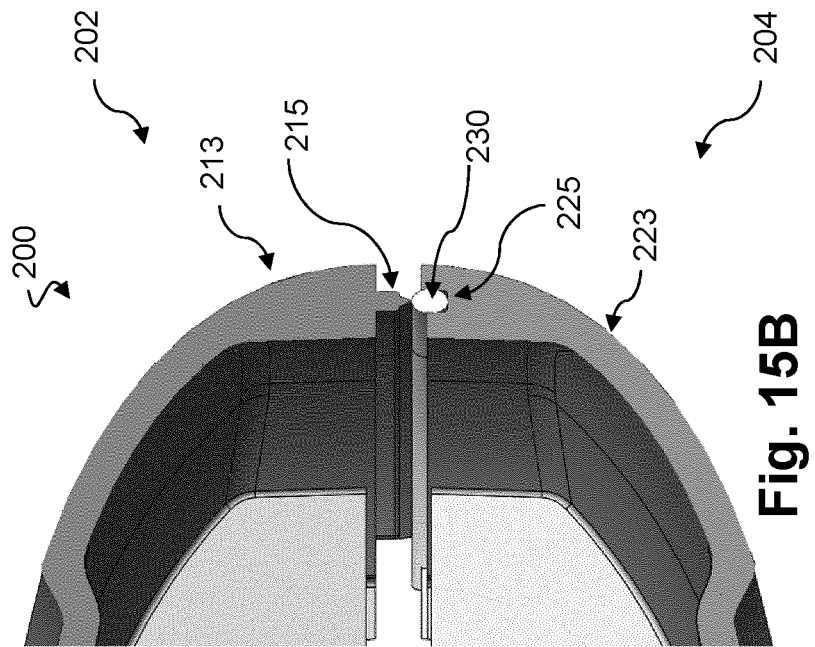
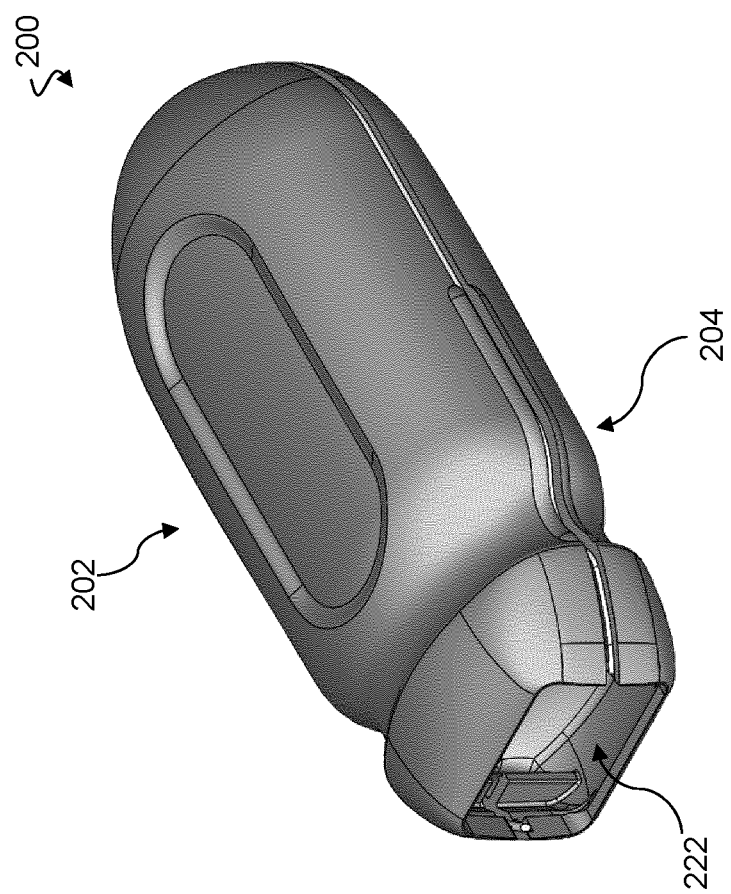
Fig. 15A
Fig. 15B

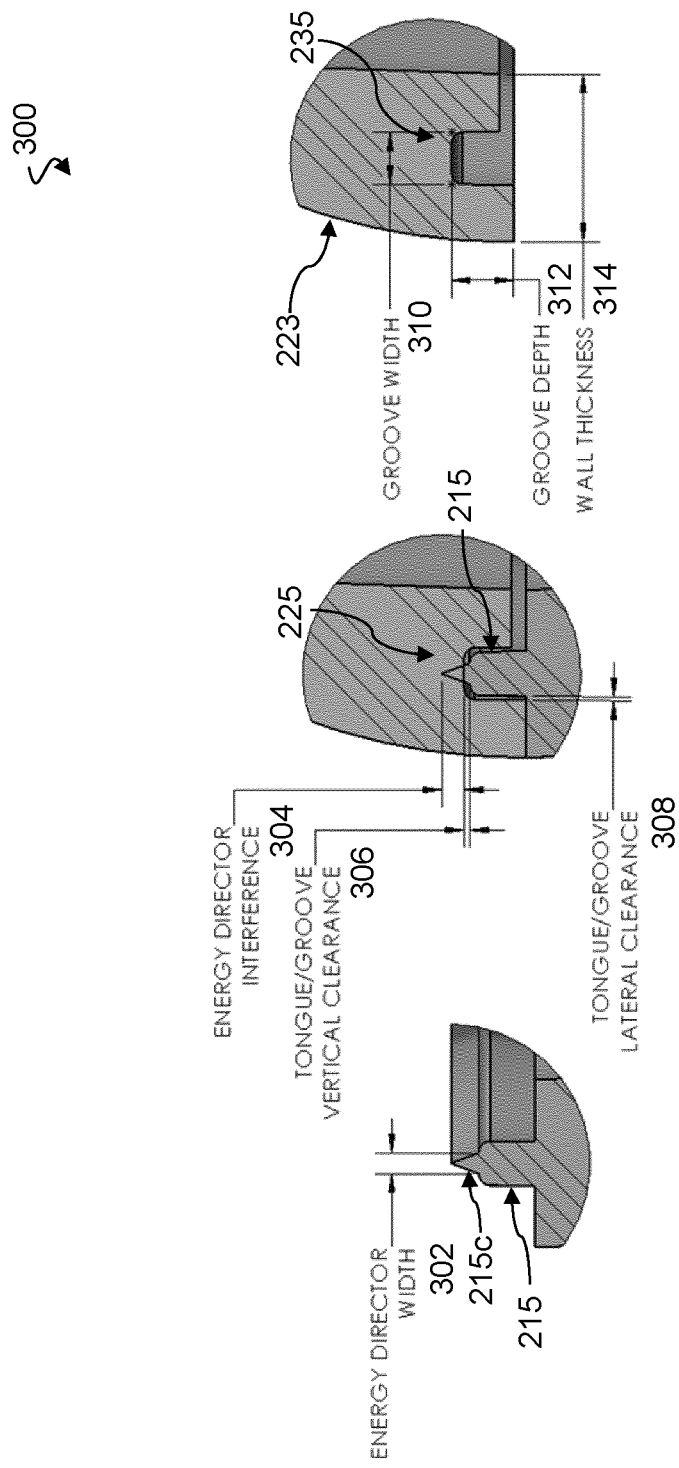

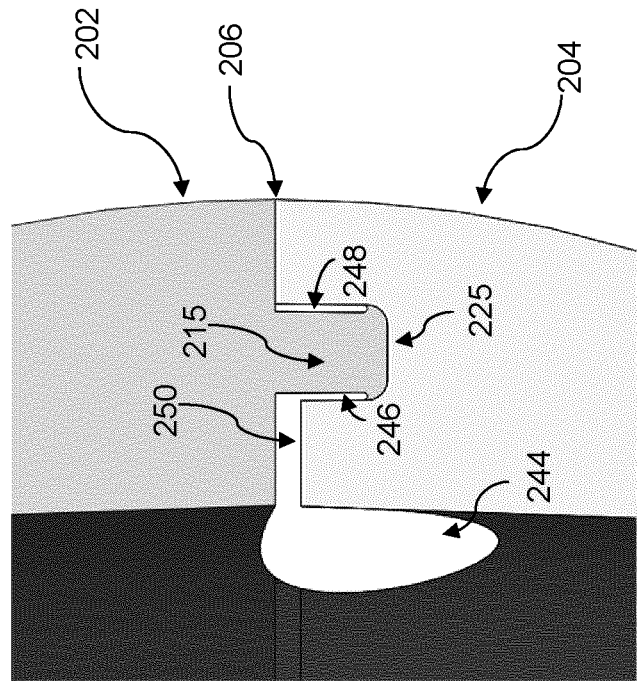
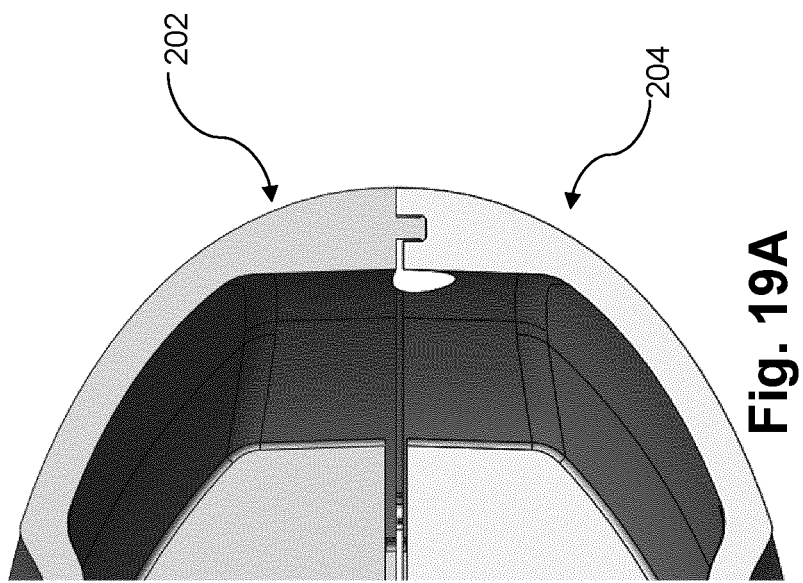
Fig. 19B
Fig. 19A

ULTRASOUND PROBE HANDLE

CROSS-REFERENCE TO PRIOR APPLICATIONS

This application is the U.S. National Phase application under 35 U.S.C. § 371 of International Application No. PCT/EP2020/062914, filed on May 8, 2020, which claims the benefit of U.S. Provisional Patent Application No. 62/846,929, filed on May 13, 2019. These applications are hereby incorporated by reference herein.

TECHNICAL FIELD

The present disclosure relates generally to the structure of an ultrasound probe, and in particular, joining portions of the ultrasound probe handle using a combination of ultrasonic welding and a sealant, such as room temperature vulcanized silicone rubber (RTV).

BACKGROUND

Diagnostic and therapeutic medical device handles have been developed with specific requirements for use in medical environments. For example, ultrasound probes require handles to meet high cosmetic and ergonomic standards. These handles are also required to be fully sterilizable as they are used with patients in medical environment. Some ultrasound probes specialized handles which have been developed over many years due to these specific requirements. However, the specialized requirements of ultrasound probe handles present manufacturing challenges, such as high scrap rates due to cosmetic or ergonomic failures and high overall cost. In particular, reliability testing of ultrasound probe handles has revealed problems in joining portions of the handles together at bondlines (also referred to as seams or parting lines) that impact the overall strength of handles and are a common source of cosmetic or ergonomic failures.

Current systems and methods to produce ultrasound probe handles have not been sufficient to adequately improve bondline failures or have imposed additional undesirable manufacturing process or reliability complications. For example, bondline failures have been observed in handles using room temperature vulcanized silicone rubber (RTV) as a gap-filler, especially in ultramobile, sealed transducers. While the addition of epoxy-bonded ribs may help to improve bondline strength for ultrasound probe handles, it is only available at discrete locations of the handle, and it is associated with additional manufacturing process complexity and manufacturing time. Additionally, physical joining or fusing techniques may pose additional challenges, such as damage to sensitive electronics or regions of failure.

SUMMARY

Methods for joining portions of a medical device handle, as well as associated devices and systems, are provided by the present disclosure. The medical device handle may be an ultrasound probe handle formed from two or more portions, such as a male portion and a female portion including tongue and groove features, respectively. The portions may be joined along a bondline using a sealant. In some embodiments, sealant such as RTV is applied to one or more portions before they are joined using an ultrasonic welding technique. As the portions are joined, the sealant may be displaced from the welding site, providing an additional sealing mechanism. Technical advancements described herein include an ultrasound probe handle with improved cosmetic and ergonomic properties. Users, such as clinicians, consider cosmetic and ergonomic properties of the ultrasound probe as indicators of quality. Improvements in the cosmetic and ergonomic properties thus result in higher quality ultrasound probes. The ultrasound probe handle may also be manufactured more efficiently than current methods by reducing scrap rates.

A method of forming an ultrasound probe is provided, which may include: applying a sealing material in a groove formed in an edge of a female portion of a housing configured to be grasped by a hand of a user; aligning an energy director extending from an edge of a male portion of the housing with the groove of the female portion; coupling the male and female portions using ultrasonic welding, wherein the coupling comprises: driving the energy director of the male portion into the groove of the female portion; fusing a portion of the energy director with a portion of the groove of the female portion; and sealing a seam formed by coupling the male and female portions using the sealing material displaced from the groove.

In some embodiments, the male portion and the female portion comprise a plastic material. the sealing material may include room temperature vulcanized silicone rubber (RTV). In some embodiments, the coupling step further includes displacing the RTV from out of the groove such that a layer of RTV is disposed on an interior surface and an exterior surface of the coupled male and female portions. The method may include removing a portion of the displaced RTV from the exterior surface of the coupled male and female portions. In some embodiments, a portion of RTV is disposed within a space between opposing walls of the energy director and the groove after the coupling step. The energy director may include a tapered distal portion. The method may include fusing the tapered distal portion of the energy director to a bottom portion of the groove.

An ultrasound probe is also provided, which may include: a housing configured to be grasped by a hand of a user, the housing comprising: a male portion comprising a curved upper portion and a lower edge, wherein an energy director extends out from the lower edge; and a female portion comprising a curved lower portion and an upper edge, wherein a groove is formed in the upper edge, wherein the energy director and the groove are welded together and form a seam such that the male and female portions together form the housing; a sealing material disposed around the welded energy director and groove to form a seal around the seam; and a transducer coupled to the housing and configured to obtain ultrasound data.

In some embodiments, the male and female portions include a plastic material. The sealing material may include room temperature vulcanized silicone rubber (RTV). The RTV may be disposed on an interior surface of the seam. The RTV may be disposed on an exterior surface of the seam. The RTV may be disposed within a space between opposing walls of the energy director and the groove. The housing may include a first opening at a distal end of the housing and a second opening at a proximal end of the housing. The seam may extend between the first opening and the second opening along a length of the housing.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 4A is a front view of the male portion of the ultrasound probe handle according to embodiments of the present disclosure.

FIG. 4B is a side view of the male portion of the ultrasound probe handle according to embodiments of the present disclosure.

FIG. 9A is a front view of the female portion of the ultrasound probe handle according to embodiments of the present disclosure.

FIG. 9B is a side view of the female portion of the ultrasound probe handle according to embodiments of the present disclosure.

FIG. 15A is a perspective view of a step to align portions of the ultrasound probe handle according to aspects of the disclosure.

FIG. 15B is a magnified cutaway view of the step to align portions of the ultrasound probe handle according to aspects of the disclosure.

FIG. 17A is a cutaway view of an energy director according to aspects of the disclosure.

FIG. 17B is a cutaway view of an energy director joined with a groove according to aspects of the disclosure.

FIG. 17C is a cutaway view of a joined energy director and groove according to aspects of the disclosure.

FIG. 19A is a cutaway view of portions of the ultrasound probe handle after joining according to aspects of the disclosure.

FIG. 19B is a magnified cutaway view of portions of the ultrasound probe handle after joining according to aspects of the disclosure.

DETAILED DESCRIPTION

Figure 1:
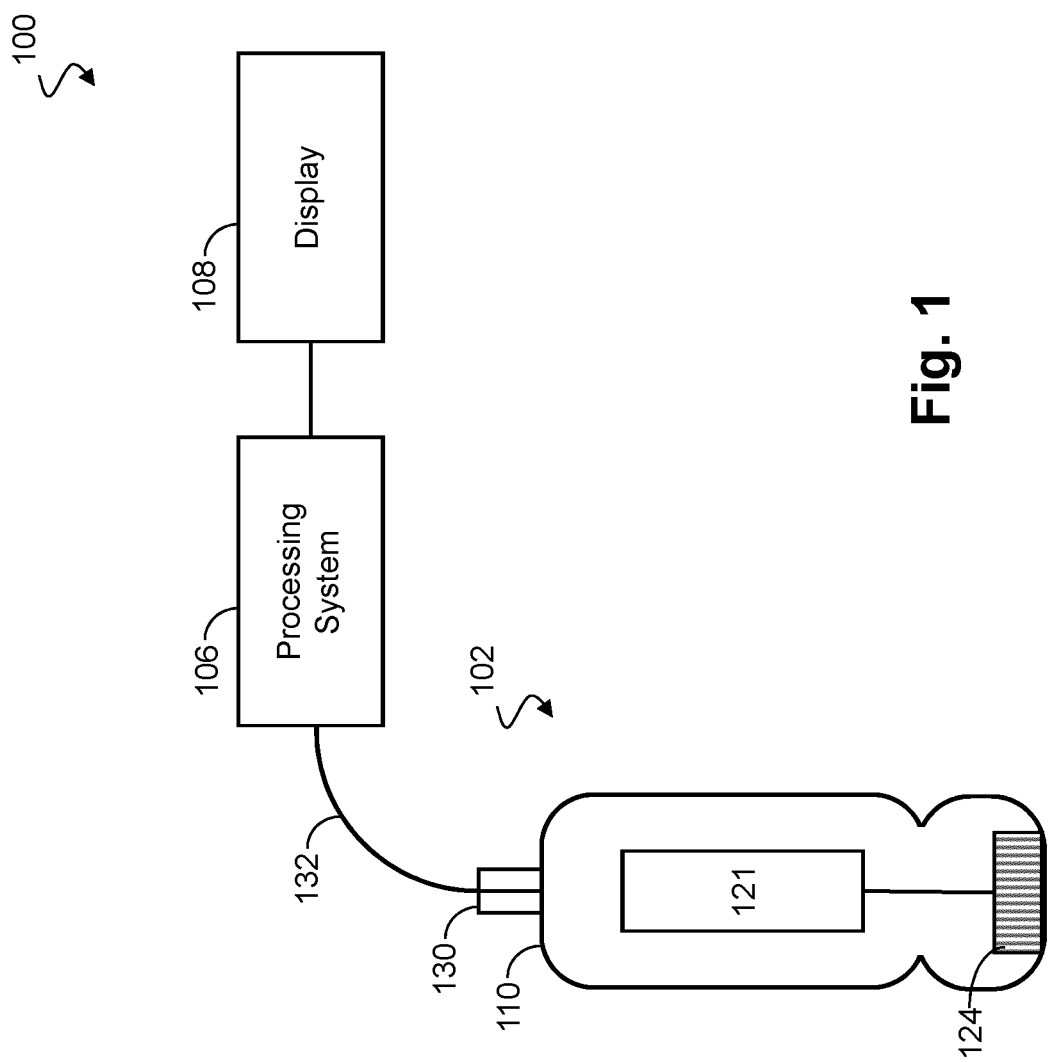
FIG. 1 is a schematic diagram of an ultrasound imaging system according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the medical device handles are discussed as ultrasound probe handles, it is understood that it is not intended to be limited to this application. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound imaging system 100, according to aspects of the present disclosure. The ultrasound imaging system 100 may include an imaging device 102, a processing system 106, and a display 108. The imaging system 100 may be used to provide non-invasive imaging of body anatomy. This imaging may include 2D or 3D B-mode ultrasonography and color flow maps. For example, the imaging device 102 is an ultrasound probe configured to visualize anatomy inside the patient's body, while the probe is positioned outside of the patient's body. In some embodiments, the ultrasound imaging system 100 is a Doppler ultrasound imaging system. In some circumstances, the system 100 may include additional elements and/or may be implemented without one or more of the elements illustrated in FIG. 1.

In some embodiments, the imaging device 102 is sized and shaped, structurally arranged, and/or otherwise configured to be placed on or near the anatomy of the subject to perform an ultrasound imaging procedure. The imaging device 102 may be positioned outside the body of a patient. In some embodiments, the device 102 is positioned proximate to and/or in contact with the body of the patient. For example, the imaging device 102 may be placed directly on the body of the subject and/or adjacent the body of the subject. For example, the imaging device 102 may be directly in contact with the body of the subject while obtaining imaging data. In some embodiments, the device 102 includes one or more imaging elements which may be placed directly on or adjacent the body of the subject. In other embodiments, a housing of the imaging device is placed directly in contact with the body of the subject such that the imaging elements are adjacent the body of the subject. The operator of the imaging device 102 may contact a distal portion of the imaging device to the body of the patient such that the anatomy is compressed in a resilient manner. The view of the anatomy shown in the ultrasound image depends on the position and orientation of the imaging device 102. To obtain imaging data of the anatomy, the imaging device 102 can be suitably positioned either manually by a clinician and/or automatically by the operator so that a transducer 124 emits ultrasound waves and receives ultrasound echoes from the appropriate portion of the anatomy. The subject may be a human patient or animal. The imaging device 102 may be portable and may be suitable to be used by a user in a medical setting. For example, the imaging device 102 may be a Doppler ultrasound imaging probe.

The imaging device 102 is configured to obtain ultrasound imaging data associated with any suitable anatomy of the patient. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, and/or other systems of the body. The anatomy may be a blood vessel, as an artery or a vein of a patient's vascular system, including cardiac vasculature, peripheral vasculature, neural vasculature, renal vasculature, and/or or any other suitable lumen inside the body. In addition to natural structures, the imaging device 102 may be used to examine man-made structures such as, but without limitation, heart valves, stents, shunts, filters and other devices.

Figure 2:
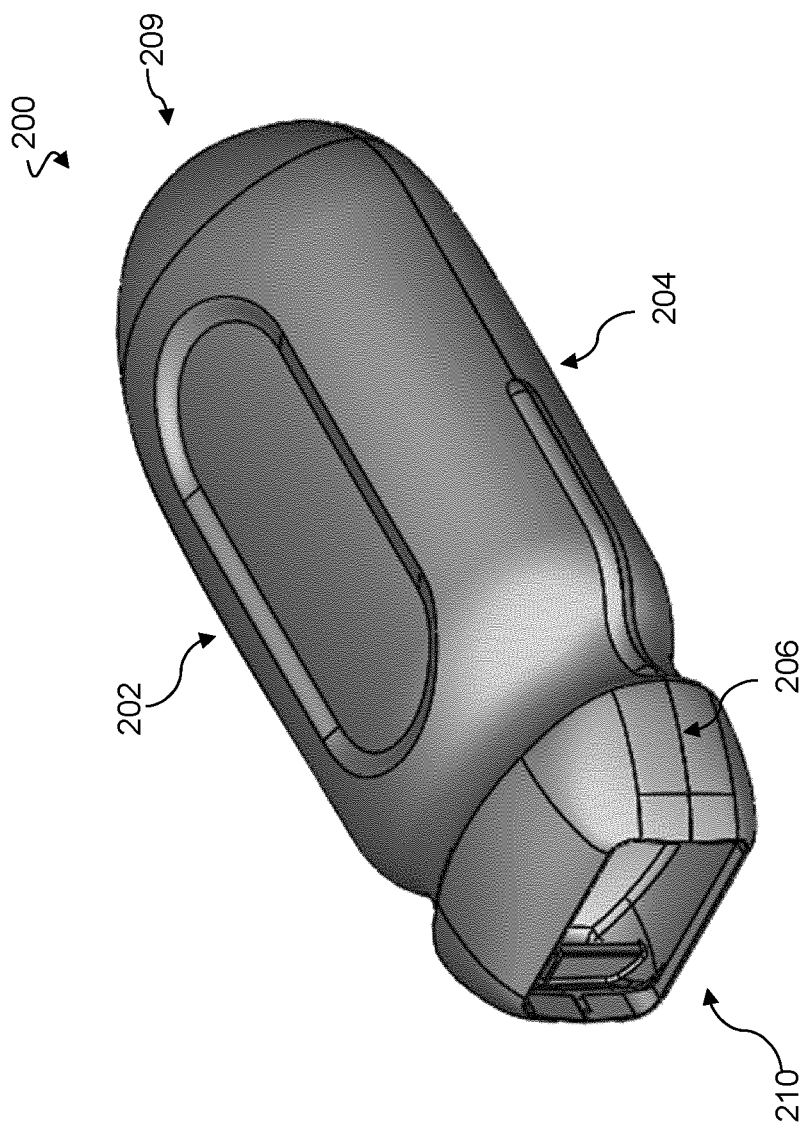
FIG. 2 is a perspective view of an ultrasound probe handle according to embodiments of the present disclosure.

The imaging device 102 may include a housing or handle 110 structurally arranged, sized and shaped, and/or otherwise configured for handheld grasping by a user. The handle 110 may be configured to surround and protect the various components of the imaging device 102, such as electronic circuitry 121 and the transducer array 124. The handle 110 may include internal structures, such as a space frame for securing the various components. For example, the transducer array may be placed at a distal portion of the handle 110, and the connector 130 at the distal portion of the cable 132 can be positioned at a proximal portion of the handle 110. In some embodiments, the handle 110 includes two or more portions which are joined together during manufacturing. For example, as shown in FIG. 2, the handle 110 may include a male portion 202 and a female portion 204 which are joined at a seam or bondline 206. In other embodiments, the handle 110 may include different numbers of components which are joined together, such as three, four or five components.

The transducer elements of the array 124 are configured to emit ultrasound signals and receive ultrasound echo signals corresponding to the emitted ultrasound signals. The ultrasound echo signals may be processed by the electronic circuitry 121 in the imaging device 102 and/or the processing system 106. The transducer array 124 can be part of an imaging assembly, including an acoustic lens and a matching material on a transmitting side of the transducer array 124, and an acoustic backing material on a backside of the transducer array 124. The transducer array 124 may include any number of transducer elements. For example, the array can include between 1 acoustic element and 1000 acoustic elements, including values such as 2 acoustic elements, 4 acoustic elements, acoustic elements, 64 acoustic elements, 128 acoustic elements, 500 acoustic elements, 812 acoustic elements, and/or other values both larger and smaller. In some instances, the transducer elements of the array may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., one or more rows, one or more columns, and/or one or more orientations) can be uniformly or independently controlled and activated. The array can be configured to obtain one-dimensional, two-dimensional, and/or three-dimensional images of patient anatomy. The ultrasound transducer elements may comprise piezoelectric/piezoresistive elements, piezoelectric micromachined ultrasound transducer (PMUT) elements, capacitive micromachined ultrasound transducer (CMUT) elements, and/or any other suitable type of ultrasound transducer elements.

The ultrasound transducer elements of the transducer array 124 are in communication with (e.g., electrically coupled to) electronic circuitry 121. The electronic circuitry 121 can be any suitable passive or active electronic components, including integrated circuits (ICs), for controlling one or more aspects associated with controlling the transducer array 124 to obtain ultrasound imaging data. For example, the electronic circuitry can include one or more transducer control logic dies. The electronic circuitry can include one or more application specific integrated circuits (ASICs). In some embodiments, one or more of the ICs can comprise a microbeamformer (μBF). In other embodiments, one or more of the ICs comprises a multiplexer circuit (MUX). In some instances, the electronic circuitry 121 can include a processor, a memory, a gyroscope, and/or an accelerometer.

The device 102 may be in communication to the computer or processing system 106 via connection cable 132. For example, conductors of the connection cable 132 can be in communication with the electronic circuitry 121 and/or the transducer array 124. The connection cable 132 may be connected to the device 102 via a connector 130 on a proximal portion of the device 102. The connection cable 132 may be any type of wired connection, such as a USB or Ethernet cable. In other embodiments, the device 102 is connected to the processing system 106 and/or display 108 via a wireless connection. In this case, the device 102 may include one or more wireless transmission devices, such as antennae. The one or more antennae may be disposed at a distal portion or a proximal portion of the device 102.

The processing system 106 is configured to perform one or more processing steps to generate an ultrasound image and output the ultrasound image for display by the display 108. One or more image processing steps completed by processing system 106 and/or a processor of the imaging device 102. The processing system 106 and/or the imaging device 102 can include one or more processors in communication with memory. The processor may be an application-specific integrated circuit (ASIC), a field-programmable gate array (FPGA), a central processing unit (CPU), a digital signal processor (DSP), another hardware device, a firmware device, or any combination thereof configured to perform the operations described herein. In some embodiments, the memory is a random access memory (RAM). In other embodiments, the memory is a cache memory (e.g., a cache memory of the processor), magnetoresistive RANI (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In some embodiments, the memory may include a non-transitory computer-readable medium. The memory may store instructions. The instructions may include instructions that, when executed by a processor, cause the processor to perform operations described herein with reference to the processor in connection with embodiments of the present disclosure.

The system 100 may be deployed in a medical setting, such as procedure room, catherization laboratory, operating room, emergency room, etc. The device 102 can be deployed adjacent to or in contact with the patient. The processing system 106 may be located near to the patient, e.g., in the same room as the patient. The processing system 106 can be remote from the patient, such as in a different room or different building. The medical setting may be used to perform any number of medical imaging procedures such as Doppler ultrasound imaging, angiography, fluoroscopy, computed tomography (CT), magnetic resonance imaging (MRI), intravascular ultrasound (IVUS), virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), intracardiac echocardiography (ICE), forward-looking ICE (FLICE), intravascular palpography, transesophageal ultrasound (ILE), and other medical imaging modalities, or combinations thereof.

The imaging device 102 and display 108 may be communicatively coupled directly or indirectly to the processing system 106. These elements may be communicatively coupled to the processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

FIG. 2 shows a medical device handle 200 which includes a male portion 202 and a female portion 204 joined together along a seam or bondline 206. The male portion 202 and female portion 204 are referred to in this way for ease of reference, however, the portions 202, 204 may be distinguished in other ways, such as first and second portions, upper and lower portions, etc. In some embodiments, the male portion 202 and female portion 204 are configured to be joined together with a tongue and groove type connection. In particular, the male portion 202 may include an extension, projection, or energy director and the female portion 204 may include a groove, recess, or opening. However, the portions 202, 204 may be joined in other ways, such as adhesive joining of substantially similar surfaces on both portions 202, 204. Furthermore, although the handle 200 is shown as formed from two portions 202, 204 that are relatively equal in size, it is understood that other numbers of portions (i.e., three, four, or five portions) with various sizes may be used to form the handle 200. The portions 202, 204 may be formed from a plastic or polymer material. For example, the portions 202, 204 may include acrylonitrile butadiene styrene (ABS), polysulfone (PSU), and polybutylene terephthalate (PBT). In some embodiments, the material can include glass fibers.

The handle 200 may be sized and shaped similarly to the handle 110 as discussed in FIG. 1. The handle 200 may include an opening at a distal end 210 (i.e., for a transducer assembly) and an opening at a proximal end 209 (i.e., for a data interface such as a connector or wires, such as the connector 130 and/or cable 132). In an exemplary embodiment, the seam or bondline 206 extends longitudinally on both sides of the handle 200, along a length of the handle 200 from the proximal end 209 to the distal end 210. The handle 200 may be sized and shaped to be grasped by a user and used in a medical environment. The male portion 202 and female portion 204 of the handle 200 may be joined together at the bondline 206 by ultrasonic welding through a portion of sealant such as room temperature vulcanized silicone rubber (RTV), as discussed in more detail with reference to FIGS. 14A-19B. In other embodiments, other types of sealant are used, including an epoxy prior to curing. In particular, the handle 200 may be formed by introducing the sealant on one or both of the male portion 202 and the female portion 204 and using a coupling mechanism (such as ultrasonic welding) to join the portions 202, 204 through the sealant. Ultrasonic welding may include placing the male portion 202 and female portion 204 together and resonating the portions 202, 204 at ultrasonic speeds, resulting in the portions 202, 204 melting into each other to form a strong, hermetic seal. Experimentation has shown ultrasonic welding to be ideal during manufacturing and may allow for handle welding without damaging internal electronics. However, although ultrasonic welding may provide a hermetic seal at a location near the center of a handle 200 wall, areas outside the weld site may remain non-fused, providing a potential reservoir for biological contaminants or debris. Therefore, a sealant such as RTV may be introduced during the welding process, filling areas outside the weld site as well as filling potential contaminant reservoirs within the bondline 206. Other coupling mechanisms such as laser welding may also be used.

Since ultrasonic welding is not significantly impeded by the presence of RTV, nor the strength of the resulting weld interface significantly weakened by RTV, the application of RTV in this way may produce a sealed bondline 206 suitable for medical applications. In particular, the collapsing gap between the male portion 202 and the female portion 204 that occurs during the welding process may displace the RTV towards both sides of the weld site, filling any imperfections within the bondline 206. The resulting interface may exhibit a high-strength, continuous hermetic seal along the entire joint interface, paralleled by a sealed bondline 206 outboard of the weld site. The use of RTV in this way may produce desirable cosmetic and ergonomic characteristics not possible with other types of bondlines 206.

Figure 3:
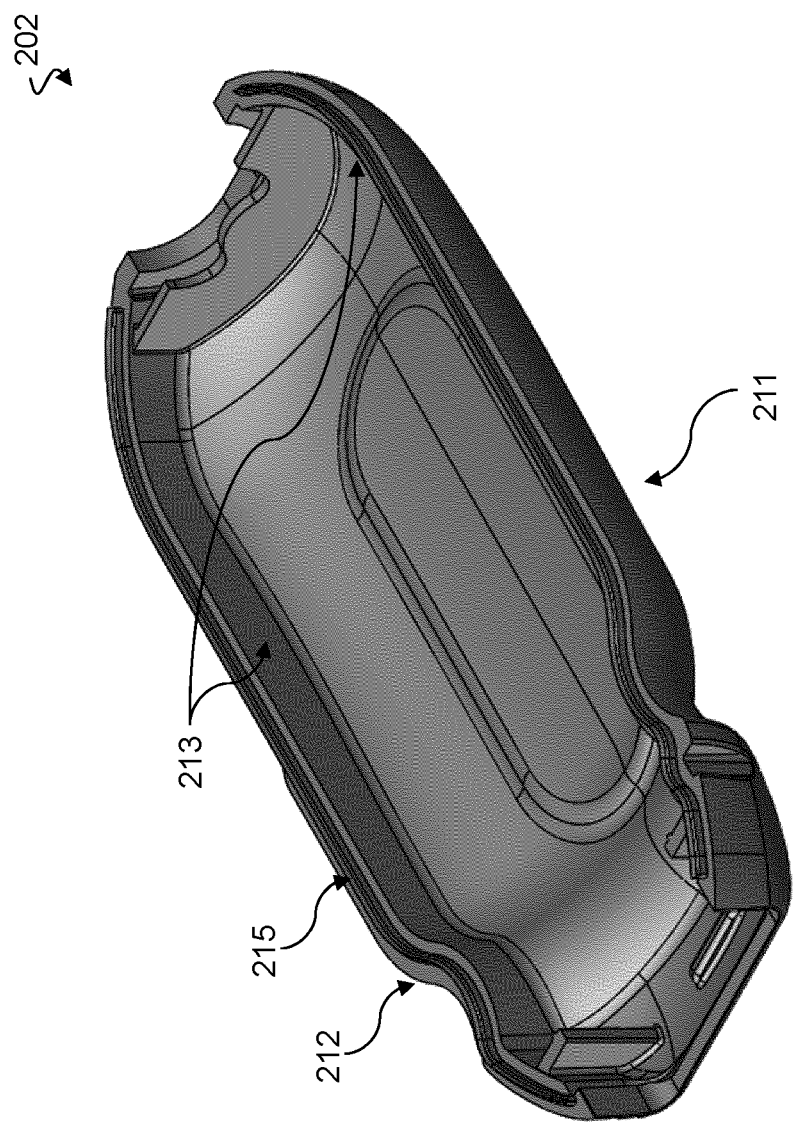
FIG. 3 is a perspective view of a male portion of the ultrasound probe handle according to embodiments of the present disclosure.

FIG. 3 shows a perspective view of the male portion 202. In some embodiments, the male portion 202 includes a curved region 211 and walls 213 that extend out from the curved region 211 to form a portion of an enclosure. The male portion 202 may include edges 212 (e.g., a first edge and an opposite, second edge on opposing sides of the male portion 202) which may include features for joining the edges 212 of the male portion 202 with edges 222 of the female portion 204. These features may tongue and groove style features for aligning and joining the portions 202, 204. In particular, the male portion 202 may include an energy director 215 (i.e., tongue) extending out from the edge 212 which is configured to fit within a groove 225 of the female portion 204. The curved region 211 of the male portion 202 may be referred to an upper portion extending down to edges 212 at a lower portion, however different terminology may be used the relative positions of these features.

FIG. 4A shows a front view of the male portion 202 showing energy directors 215 extending out from the edges 212 of the walls 213 which in turn extend out from the curved portion 211. In some embodiments, the energy directors 215 extend only around a portion of the male portion 202, such that openings are formed in the male portion 202, such as at the proximal and distal ends 209, 210. For example, the energy directors 215 may include a first energy director and a second, opposite energy director. FIG. 4B shows a side view of the male portion 202.

Figure 5:
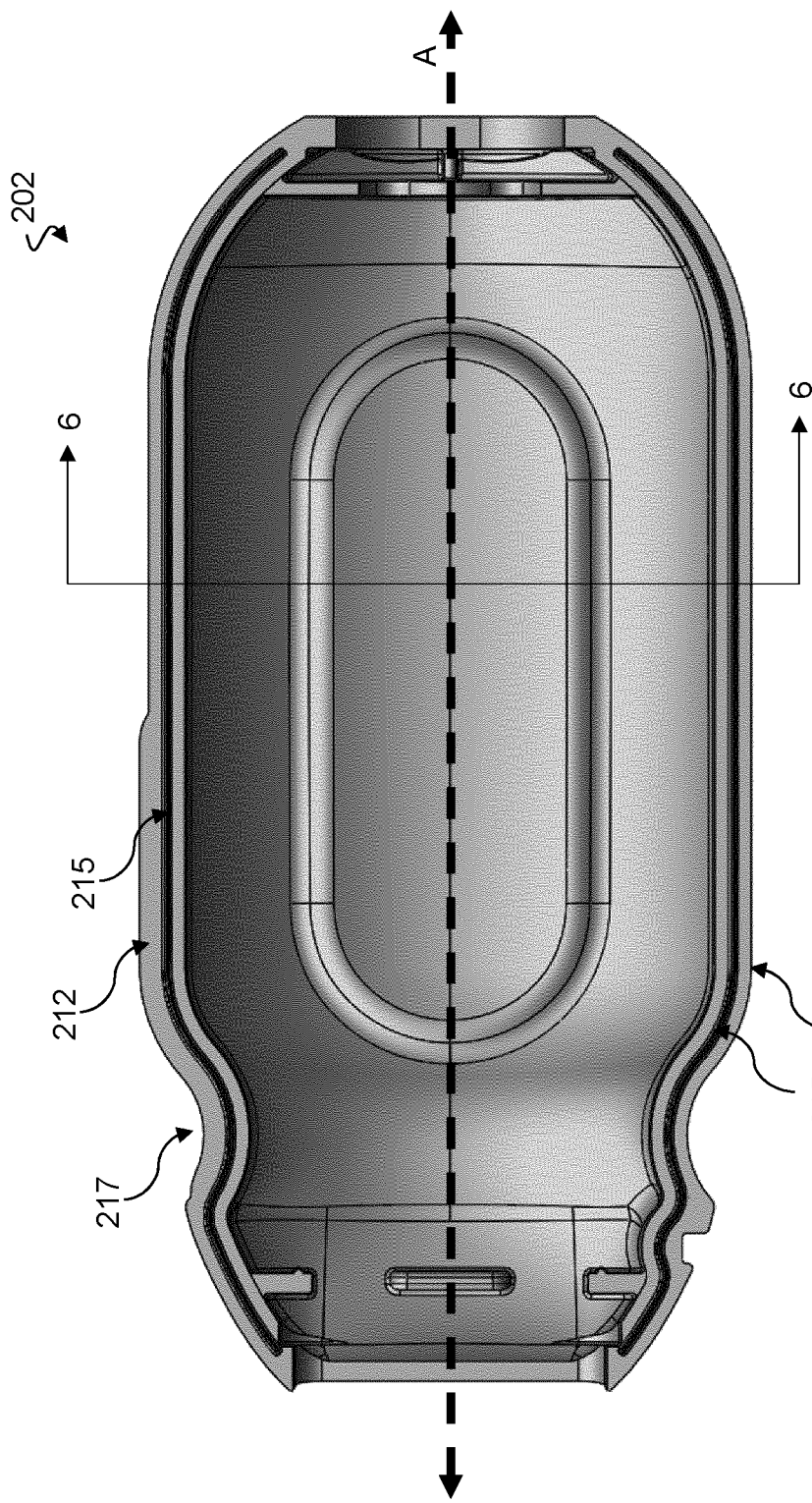
FIG. 5 is a top view of the male portion of the ultrasound probe handle according to embodiments of the present disclosure.

FIG. 5 shows a top view of the male portion 202. In some embodiments, the male portion 202 may include a notch 217 on an outer edge. The notch may facilitate gripping by a user. FIG. 5 also shows that the energy directors 215 may extend along central portions of the edge 212. The energy directors 215 may extend around opposing sections of the edges 212. In some embodiments, the edges 212 and energy directors 215 are substantially symmetrical with respect to a longitudinal axis A of the male portion 202. The edges 212 and energy directors 215 may include gently curved surfaces to facilitate comfortable handheld gripping by a user.

Figure 6:
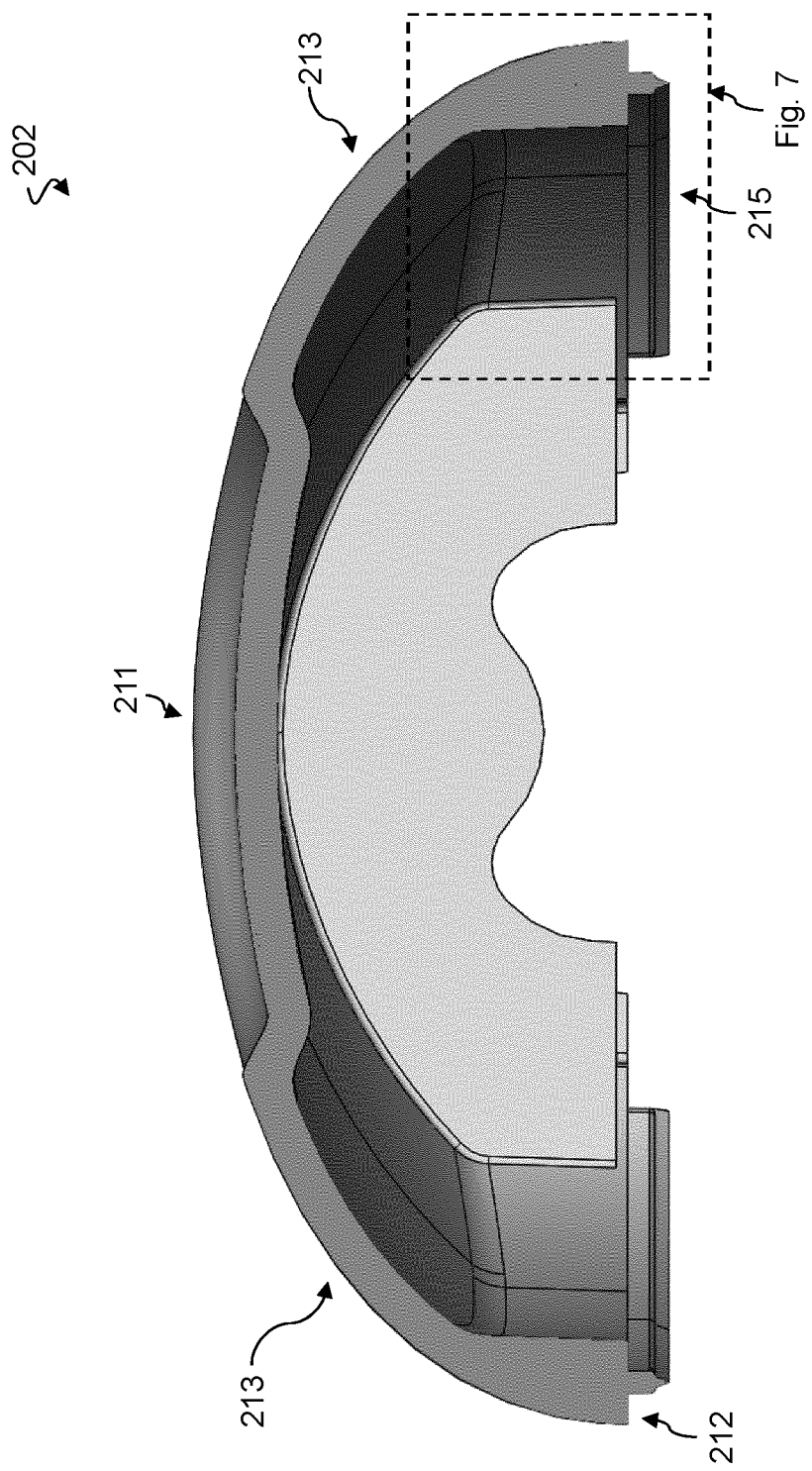
FIG. 6 is a cutaway view of the male portion of the ultrasound probe handle along section line 6-6 in FIG. 5 according to embodiments of the present disclosure.

FIG. 6 is a cutaway view of the male portion 202 along the line 6 shown in FIG. 5. The profile of the male portion 202 shows the curved portion 211 which extends with walls 213 in a continuous shape. In some embodiments, the thickness of walls 213 may increase near the edges 212. This may increase the structural strength of the handle 200.

Figure 7:
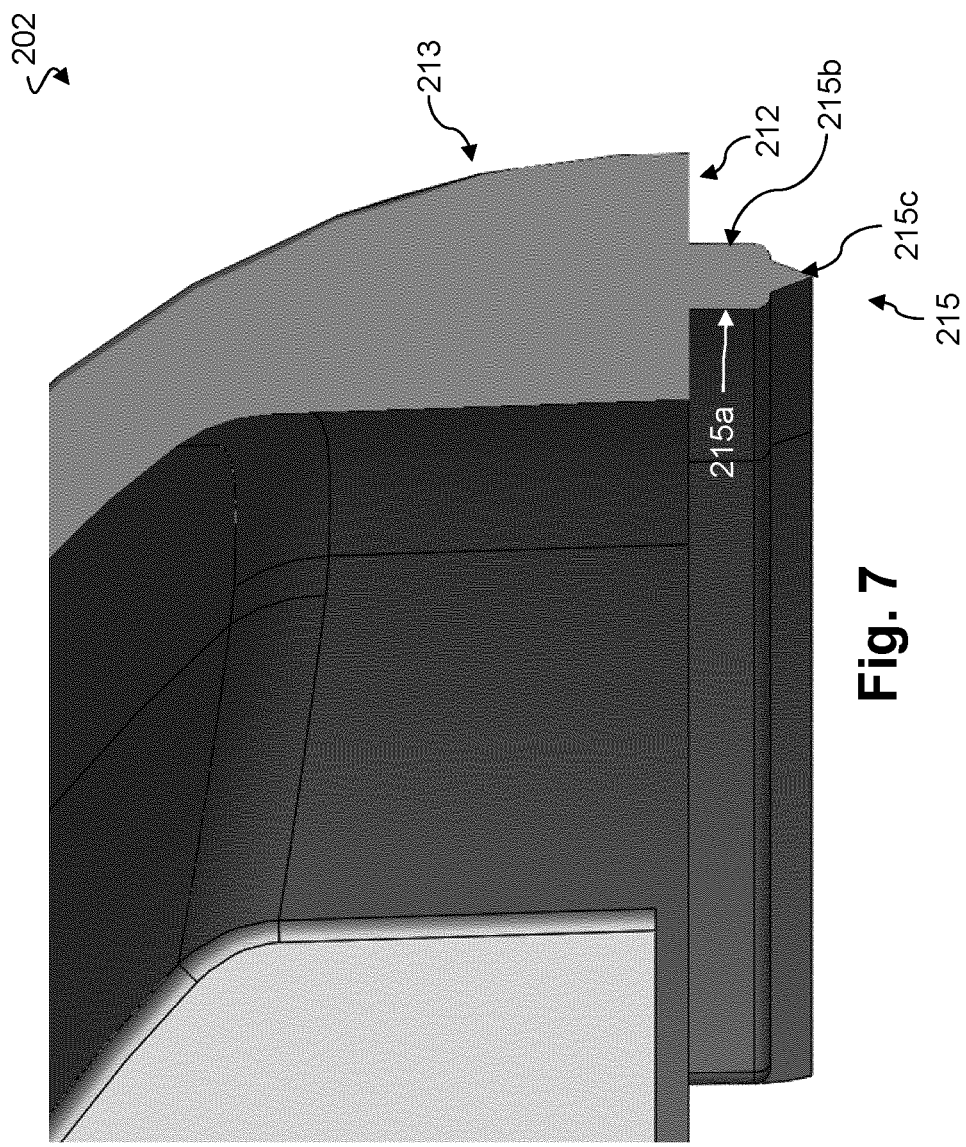
FIG. 7 is a magnified cutaway view of section 7 in of the male portion of the ultrasound probe handle in FIG. 6 according to embodiments of the present disclosure.

FIG. 7 is a magnified view of a section 7 of the male portion 202 as shown in FIG. 6. As shown in this cutaway view, the energy directors 215 may extend continuously from a surface of the edges 212. In some embodiments, the energy directors 215 may include an inner surface 215a, an outer surface 215b, and an extension 215c. In some embodiments, the inner and outer surfaces 215a, 215b are substantially planar and extend in a transverse direction with respect to the edge 212. The inner and outer surfaces 215a, 215b may include a curved portion joined at the extension 215c which may come to a point. In some embodiment, the energy directors 215 are configured to be joined or coupled with a groove of the female portion 204, as shown in FIGS. 17A-17C.

Figure 8:
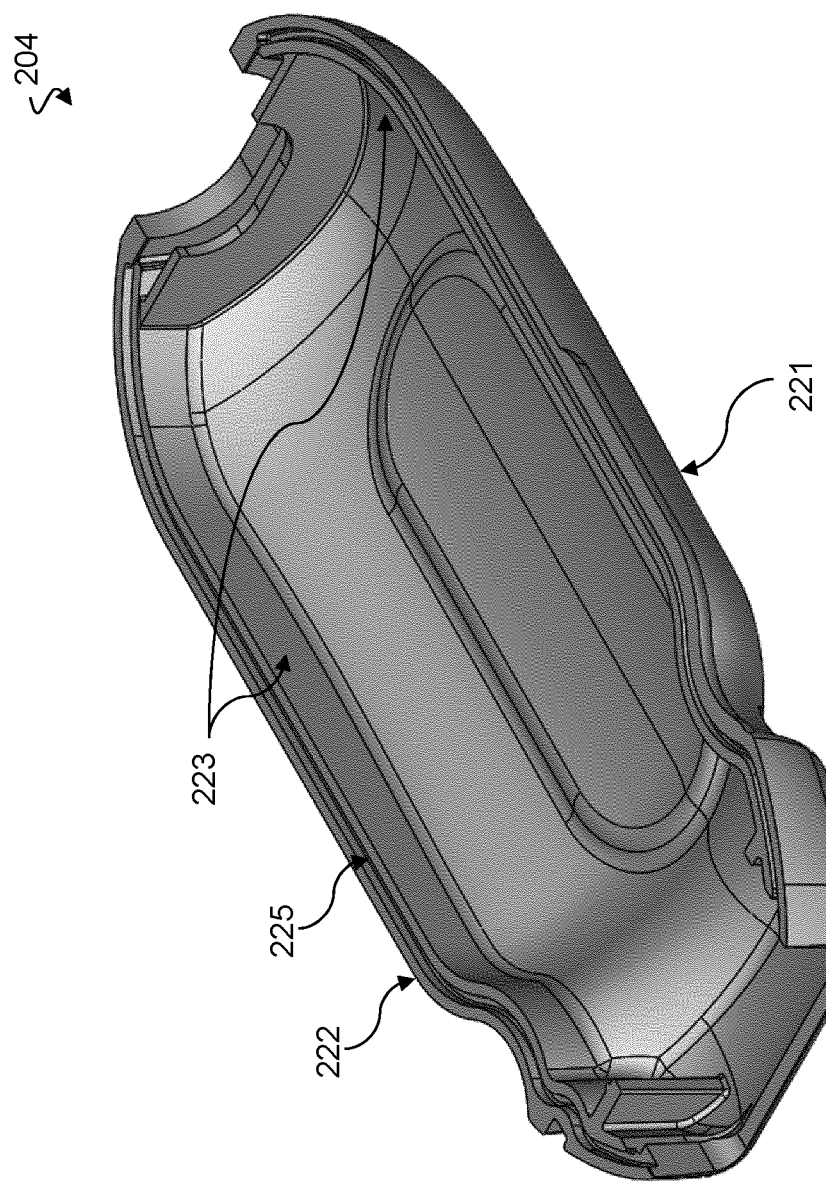
FIG. 8 is a perspective view of a female portion of the ultrasound probe handle according to embodiments of the present disclosure.

FIG. 8 shows a perspective view of a female portion 204 of the medical device handle 200. In some embodiments, the female portion 204 includes a curved region 221 and walls 223 that extend out from the curved region 221 to form a portion of an enclosure. Similar to the male portion 202, the female portion 204 includes edges 222 which may include features for joining edges 212 of the male portion 202 with edges 222 of the female portion 204. In particular, the female portion 204 may include an opening or groove 225 within the edge 222 which is configured to be coupled with an energy director 215 of the male portion 202. The curved region 221 of the female portion 204 may be referred to a lower portion extending up to edges 222 at a lower portion, however different terminology may be used the relative positions of these features.

FIG. 9A shows a front view of the female portion 204 showing the walls 223 which extend out from the curved portion 221 to the edges 222. In some embodiments, the edges 222 extend along a single plane. Similar to the male portion 202, the edges 222 and groove 225 therein may extend only around a portion of the female portion 204, such that openings are formed in the female portion 204, such as at the distal and proximal ends. FIG. 9B shows a side view of the female portion 204.

Figure 10:
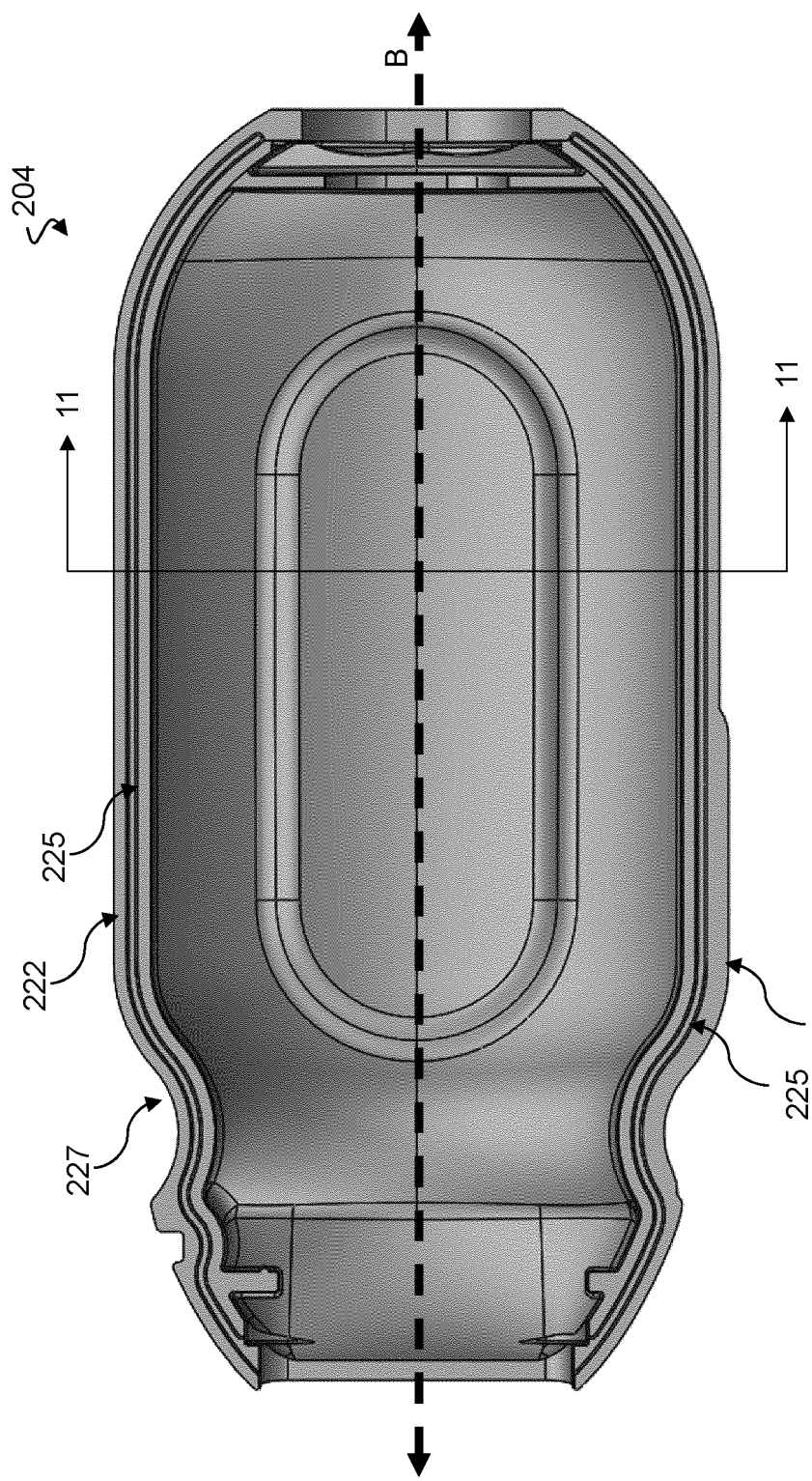
FIG. 10 is a top view of the female portion of the ultrasound probe handle according to embodiments of the present disclosure.

FIG. 10 shows a top view of the female portion 204. In some embodiments, the female portion 204 may include a notch 227 on an outer edge. The notch 227 may facilitate gripping by a user. As also shown in FIG. 8, the grooves 225 may extend out central portions of the edges 222. The grooves 225 may extend around opposing sections of the edges 222. In some embodiments, the edges 222 and grooves 225 are substantially symmetrical with respect to a longitudinal axis A of the female portion 204. Similar to the edges 212 of the male portion 202, the edges 222 of the female portion 204 may include gently curved surfaces to facilitate comfortable handheld gripping by a user.

Figure 11:
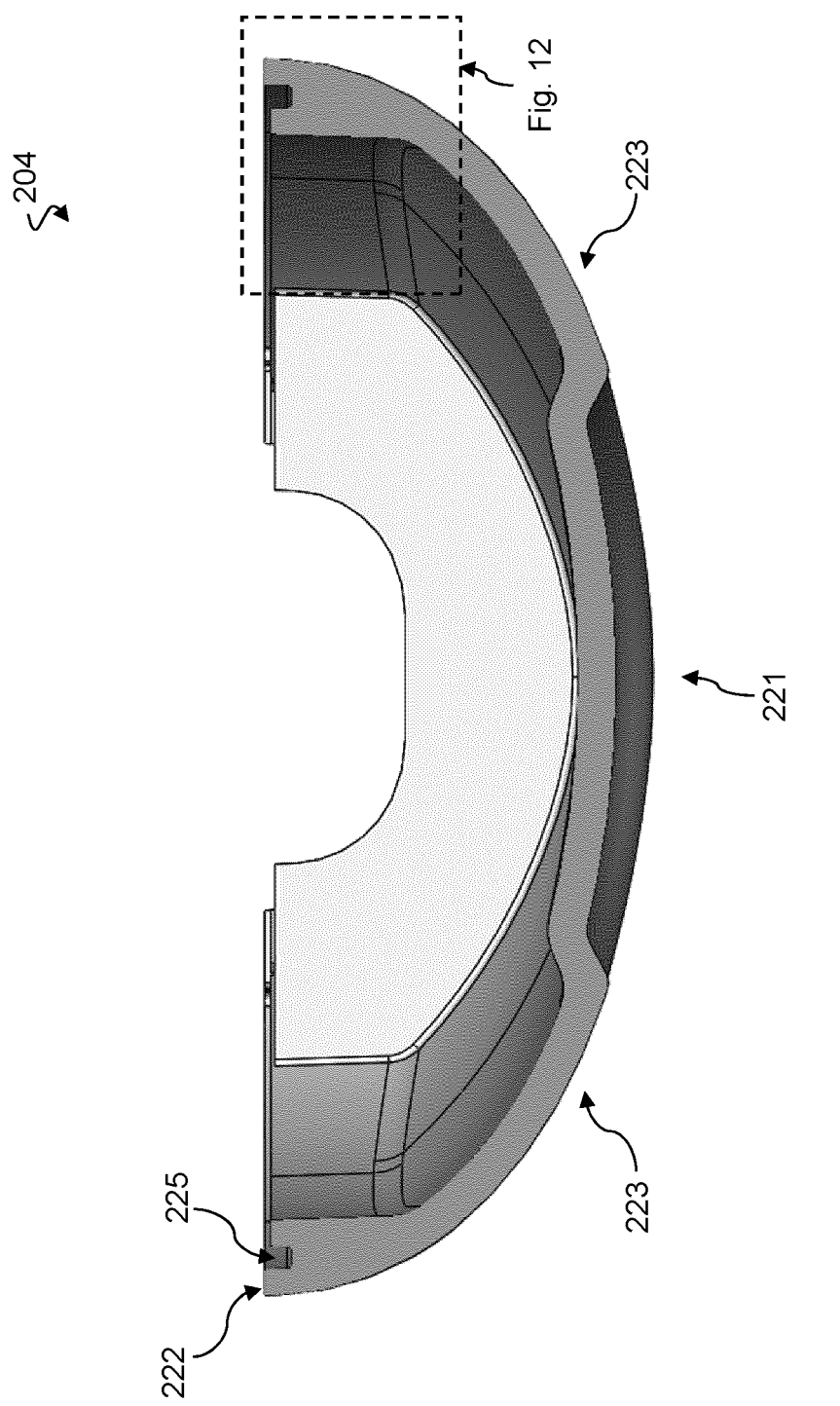
FIG. 11 is a cutaway view of the female portion of the ultrasound probe handle along section line 11-11 in FIG. 10 according to embodiments of the present disclosure.

FIG. 11 is a cutaway view of the female portion 204 along the line 11 shown in FIG. 10. The profile of the female portion 204 shows the curved portion 221 which extends with walls 223 to form a continuous shape. In some embodiments, the thickness of walls 223 may increase near the edges 222. This may increase the structural strength of the handle 200. The shape of the groove 225 can also be seen.

Figure 12:
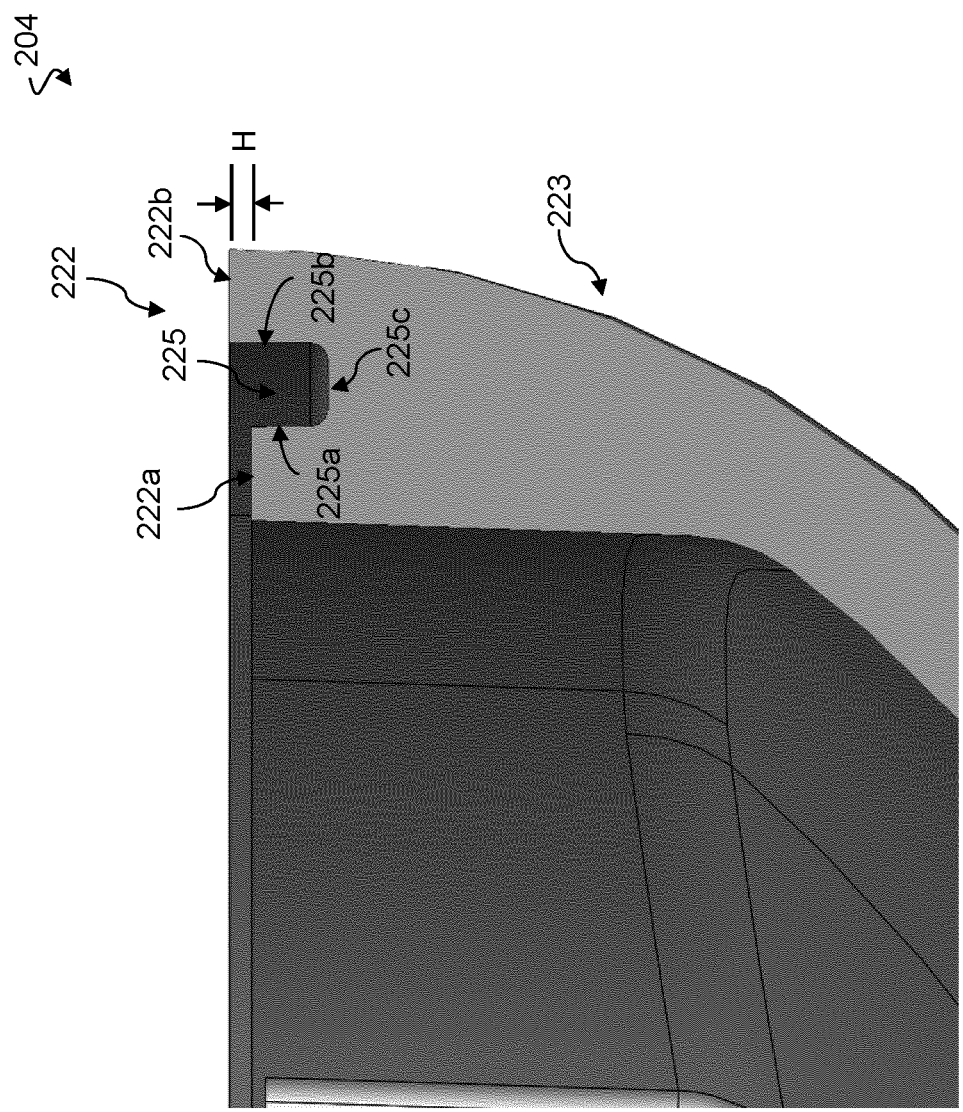
FIG. 12 is a magnified cutaway view of section 12 in of the female portion of the ultrasound probe handle in FIG. 11 according to embodiments of the present disclosure.
Figure 18B:
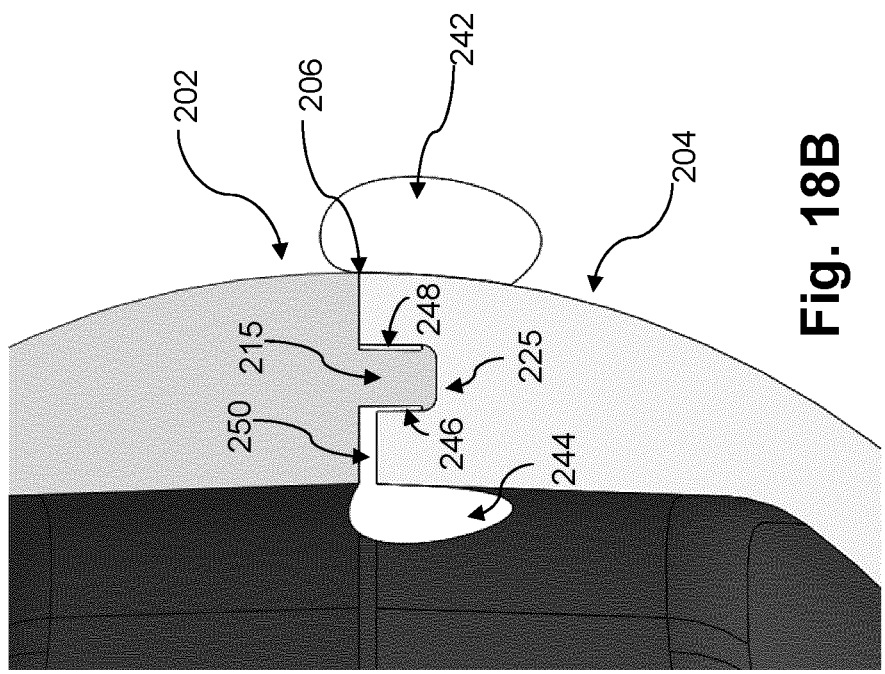
FIG. 18B is a magnified cutaway view of portions of the ultrasound probe handle after joining according to aspects of the disclosure.
Figure 18A:
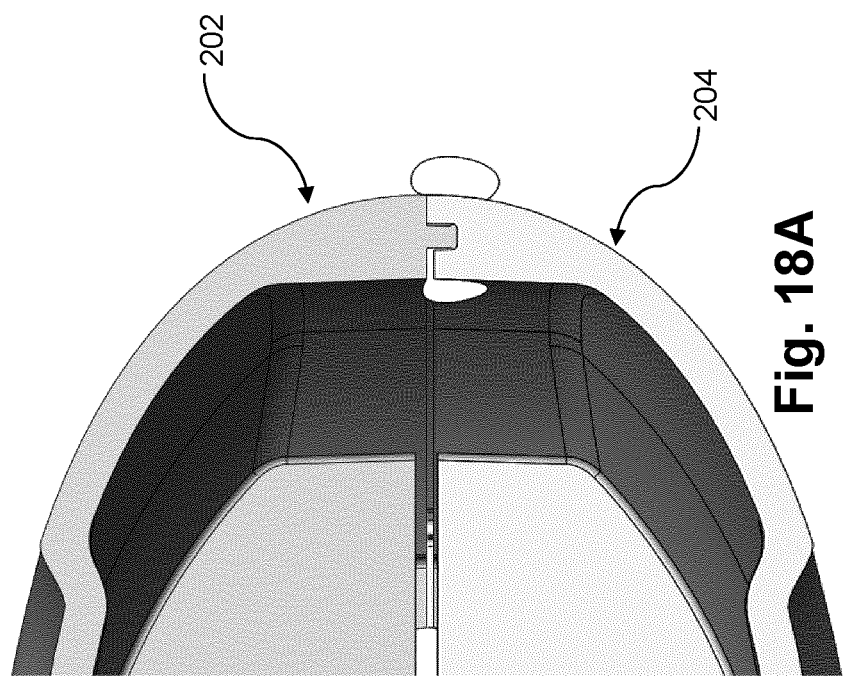
FIG. 18A is a cutaway view of portions of the ultrasound probe handle after joining according to aspects of the disclosure.

FIG. 12 is a magnified view of a section 12 of the female portion 204 as shown in FIG. 11. As shown in this cutaway view, the groove 225 may be recessed within the edges 222. The edges 222 may include one or more surfaces, such as an inner surface 222a and an outer surface 222b. In some embodiments, the inner surface 222a has a top horizontal surface that is lower than a top horizontal surface of the outer surface 222b. This difference may be shown by height H as shown. This may facilitate the flow of sealant 230 to an inner surface of the handle 200 when the male and female portions 202, 204 are joined together, as shown in FIGS. 18A and 18B. In other embodiments, the edges 222 include a single, level surface. As shown in the example of FIG. 12, the grooves 225 may be formed in a central portion of the edges 222. In some embodiments, the grooves 225 have a substantially rectangular profile with a substantially vertical inner wall 225a, a substantially vertical outer wall 225b that may be parallel to the inner wall 225a, and a horizontal straight or curved bottom 225c that extends between the inner wall 225a and the outer wall 225b. In other embodiments, the grooves 225 have different shapes, such as having curved or polygonal profiles with two or more surfaces. The energy directors 215 of the male portion 202 may be joined with the grooves 225, as shown in FIGS. 17A-17C.

Figure 13:
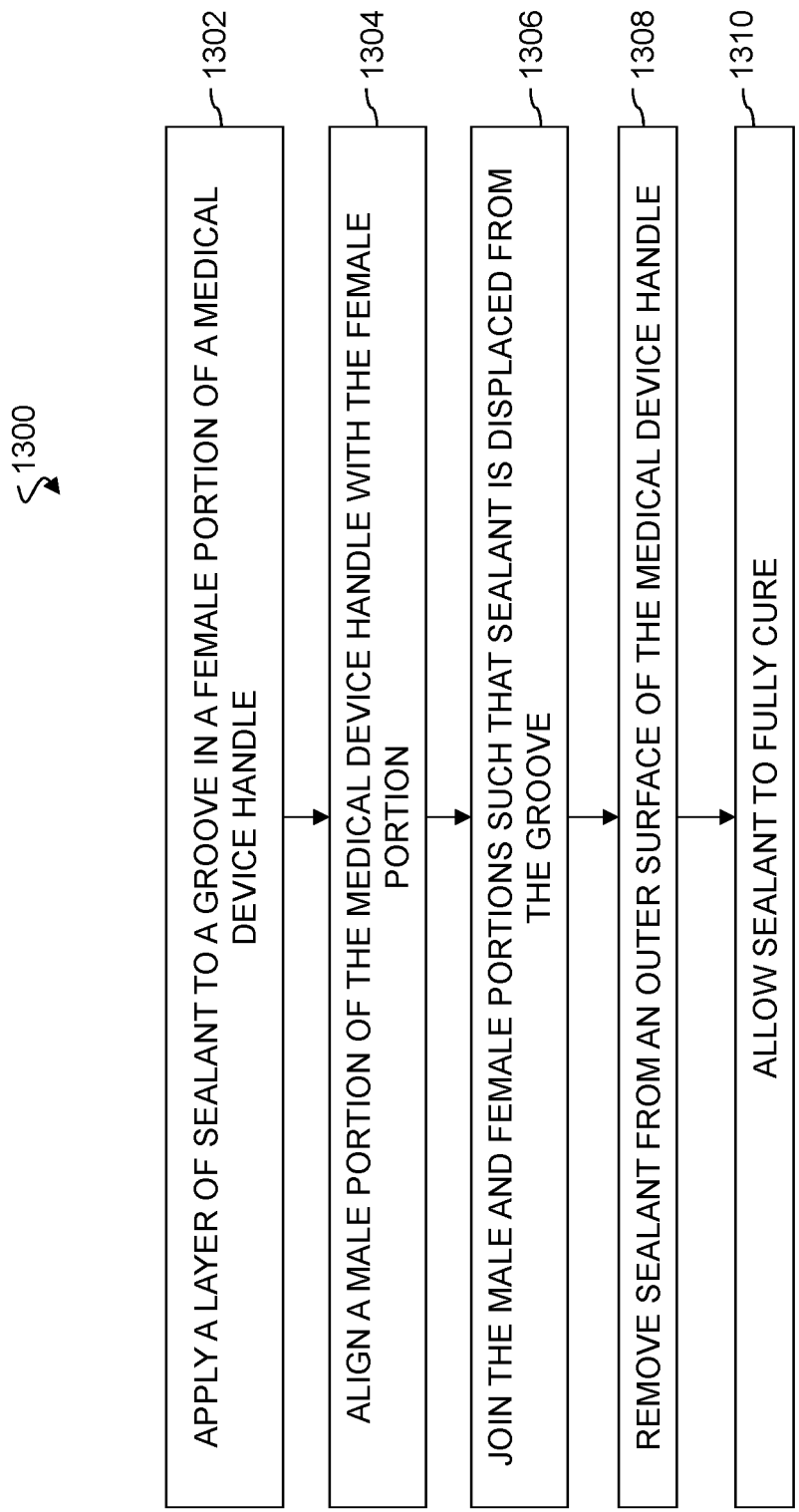
FIG. 13 is a flow diagram of a method of forming an ultrasound probe handle according to aspects of the disclosure.
Figure 14B:
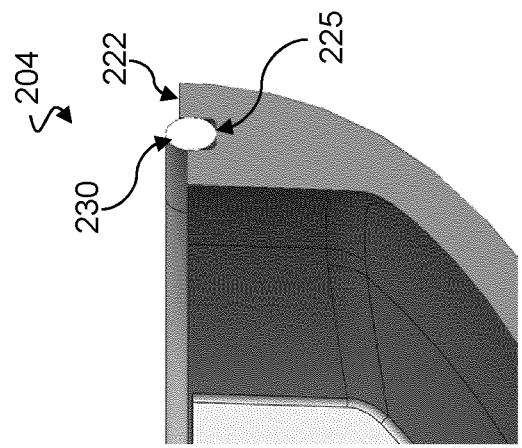
FIG. 14B is a magnified cutaway view of the step to apply sealant to a portion of the ultrasound probe handle according to aspects of the disclosure.
Figure 14A:
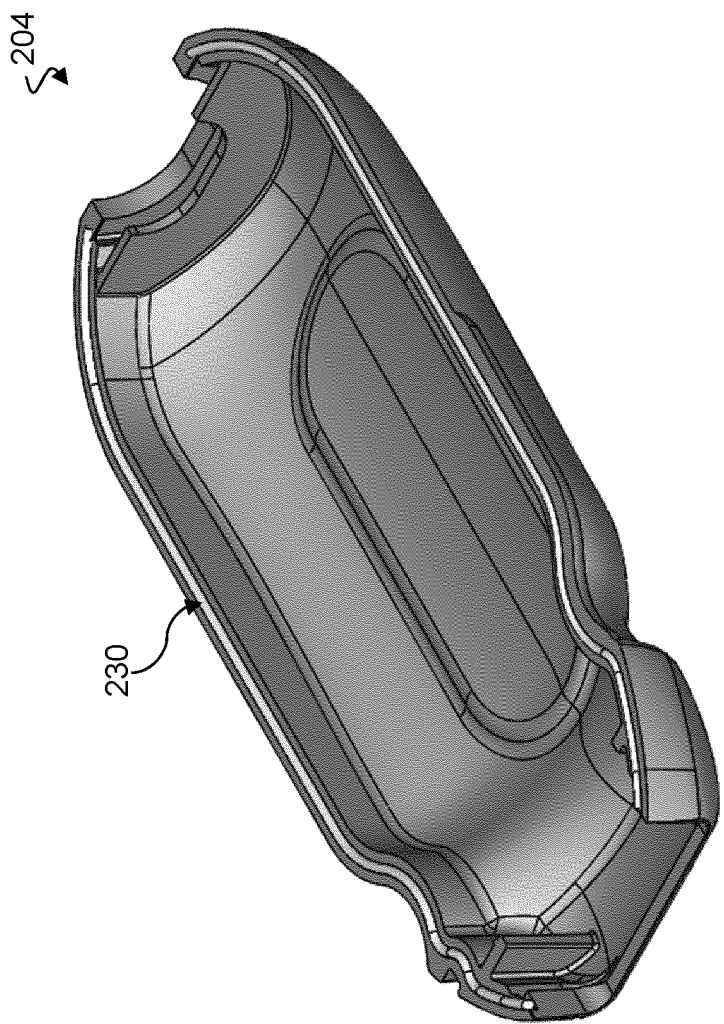
FIG. 14A is a perspective view of a step to apply sealant to a portion of the ultrasound probe handle according to aspects of the disclosure.

FIG. 13 illustrates a flow diagram illustrating an exemplary method 1300 of forming a medical device handle by joining two or more portions together. The steps of the method 1300 are shown with reference to FIGS. 14A-19B. At step 1302, the method 1300 may include applying a layer of sealant 230 to a groove 225 in a female portion 204 of a medical device handle 200. As shown in FIGS. 14A and 14B, sealant 230 such as RTV may be applied to the groove 225. In some embodiments, the sealant 230 is applied in a line or bead such that it fills the groove 225 and even extends out of the groove 225 such that the sealant 230 rises above the edges 222 of the female portion 204.

Figure 16B:
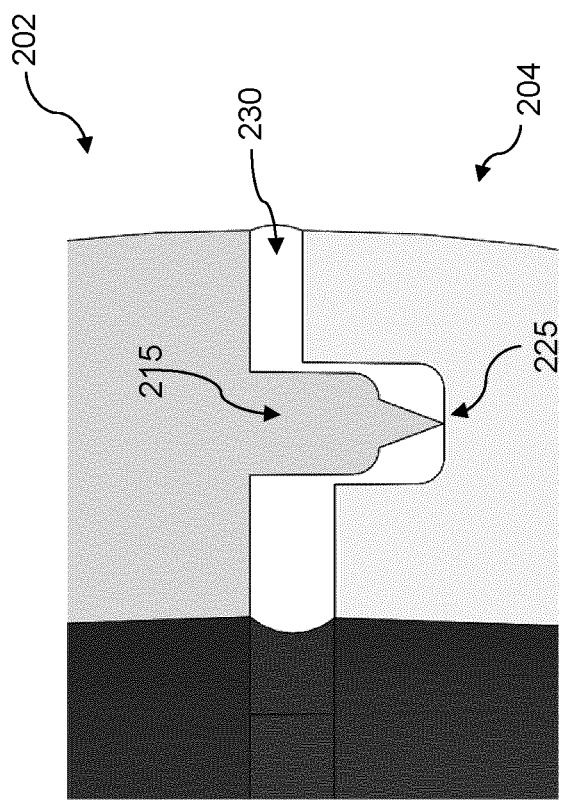
FIG. 16B is a magnified cutaway view of the step to align portions of the ultrasound probe handle according to aspects of the disclosure.
Figure 16A:
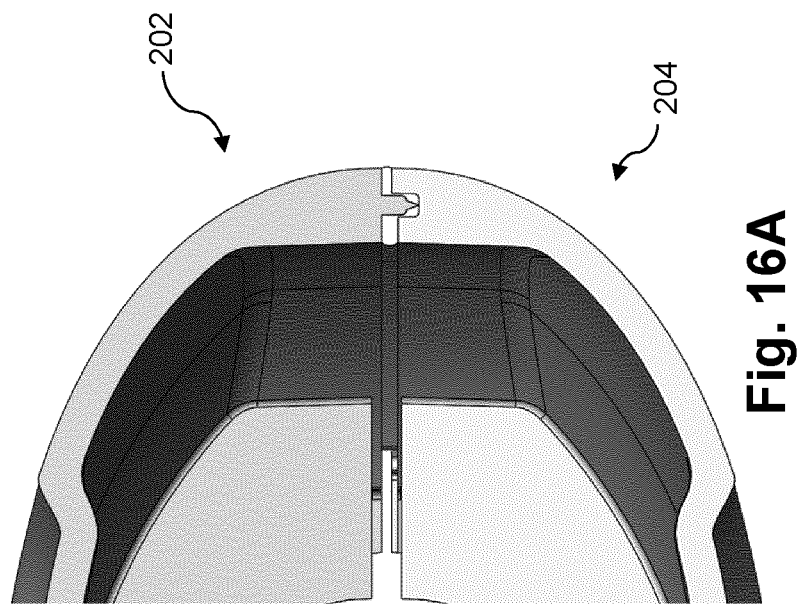
FIG. 16A is a cutaway view of a step to align portions of the ultrasound probe handle according to aspects of the disclosure.

At step 1304, the method 1300 may include aligning a male portion 202 of the medical device handle 200 with the female portion 204. As shown in FIGS. 15A and 15B, the alignment of the male and female portions 202, 204 may include aligning features such as walls 213, 223. The energy director 215 of the male portion 202 may be aligned with the groove 225 of the female portion 205 in preparation for joining the male portion 202 to the female portion 204. Once aligned, the energy director 215 is placed within the groove 225, displacing a portion of the sealant 230, as shown in FIGS. 16A and 16B. The sealant 230 is further displaced as the male and female portions 202, 204 are joined, as shown in FIGS. 18A, 18B, 19A, and 19B.

At step 1306, the method 1300 may include joining the male and female portions 202, 204 of the handle 200 such that the sealant 230 is displaced from the groove 225, as shown in FIGS. 17A-18B. This step 1306 may include pressing the male and female portions 202, 204 together and coupling them, such as by ultrasonic welding. As shown in FIG. 17A, the extension 215c of the energy director 215 may have a first width 302. In some embodiments, the energy director 215 is joined with a bottom surface 225c of the groove 225 such that the extension 215c of the energy director 215 is heated, melted, and fused with the bottom surface 225c of the groove 225, as shown in FIG. 17B. The welding of the energy director 215 and groove 225 may create the energy director interference 304 and leave a vertical clearance 306 and lateral clearance 308 between the energy director 215 and groove 225. As shown in FIG. 17C, after joining the energy director 215 and groove 225, the joined groove 235 may have a second width 310 and a first depth 312 with a thickness 314 of the wall 223 also shown.

FIGS. 18A and 18B show the displacement of the sealant 230 after joining the male and female portions 202, 204. In some embodiments, after displacement, the sealant 230 is displaced to a first position 242 on an outer surface of the handle 200 (such as outside the walls 213 and 223), a second position 244 on an inner surface of the handle 200, a first space 246 between the inner surface 215a of the energy director 215 and the inner wall 225a of the groove 225 (e.g., having a width equivalent to the lateral clearance 308 shown in FIG. 17B), a second space 248 between the outer wall 215b of the energy director 215 and the outer wall 225b of the groove 225 (e.g., having a width equivalent to the lateral clearance 308 shown in FIG. 17B), and a third space 250 between the edge 212 of the male portion 202 and the first surface 222a of the edge 222 of the female portion 204 (e.g., having a height equivalent to a height H between surfaces 222a, 222b of the edge as shown in FIG. 12. In some embodiments, the sealant 230 in the first, second, and third spaces 246, 248, 250 add strength to the bond between the male and female portions 202, 204 and may help to seal the bondline 206, such as from liquid ingress.

At step 1306, the method 1300 may include removing sealant 230 from an outer surface of the medical device handle 200. As seen in the comparison of FIGS. 18B and 19B, the sealant 230 at the first position 242 outside walls 213 and 223 of the handle 200 has been removed in FIG. 19B. In some embodiments, a small portion of the sealant 230 may be left an external portion of the bondline 206 to aid in sealing. The displaced sealant 230 may also remain in one or more of the second position 244 and first, second and third spaces 246, 248, 250.

At step 1310, the method 1300 may further include allowing the sealant 230 to fully cure. This step 1310 may include allowing the RTV to fully dry and cure.

Figure 20:
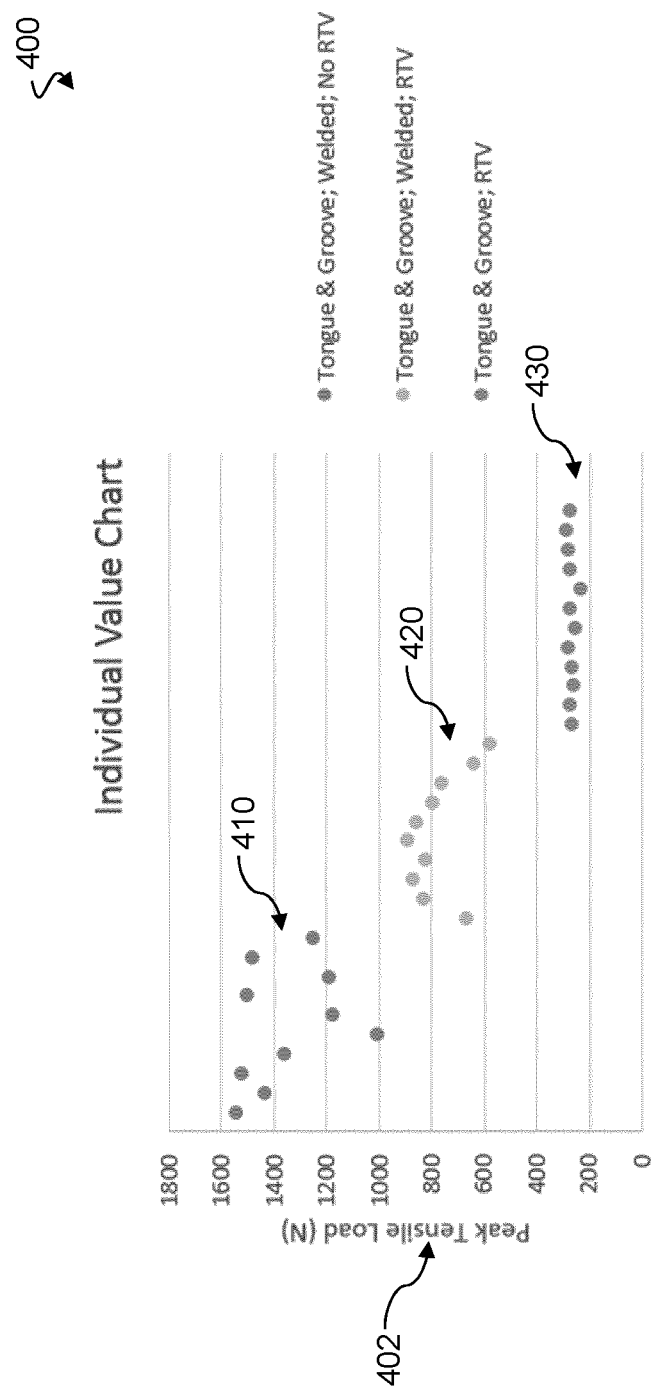
FIG. 20 is a diagram showing bond strength for different methods of joining portions of an ultrasound probe handle according to embodiments of the present disclosure.

FIG. 20 illustrates a comparison 400 of bond strength of different methods for coupling portions of the handle 200. The comparison 400 was generated based on experimental samples of the various coupling methods. Group 410 shows the bond strength of a handle 200 coupled by using a tongue and groove welding connection without RTV, and has a peak tensile load of about 1000 N to about 1600 N. Group 420 shows the bond strength of a handle 200 coupled by using a tongue and groove welding connection with RTV, and has a peak tensile load of about 580 N to about 850 N. Group 430 shows the bond strength of a handle 200 coupled by using a tongue and groove connection with RTV (without welding), and has a peak tensile load of about 210 N to about 250 N. Therefore, the welding interface with RTV has been demonstrated to be approximately 2.8 stronger than a RTV interface without welding. Although the presence of RTV reduces the weld interface strength by about a factor of 0.4, the addition of RTV substantially improves cosmetic and ergonomic factors of the handle 200.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of forming an ultrasound probe, comprising:
   applying a room temperature vulcanized silicone rubber (RTV) sealing material in a groove formed in an edge of a female portion of a housing configured to be grasped by a hand of a user;
   aligning an energy director extending from an edge of a male portion of the housing with the groove of the female portion;
   coupling the male and female portions using ultrasonic welding, wherein the coupling comprises:
      driving the energy director of the male portion into the groove of the female portion;
      fusing a portion of the energy director with a portion of the groove of the female portion;
      displacing the RTV from out of the groove such that a layer of RTV is disposed on an interior surface and an exterior surface of the coupled male and female portions; and
      sealing a seam formed by coupling the male and female portions using the sealing material displaced from the groove.

2. The method of claim 1, wherein the male portion and the female portion comprise a plastic material.

3. The method of claim 2, wherein a portion of RTV is disposed within a space between opposing walls of the energy director and the groove after the coupling step.

4. The method of claim 1, further comprising removing a portion of the displaced RTV from the exterior surface of the coupled male and female portions.

5. The method of claim 1, wherein the energy director comprises a tapered distal portion.

6. The method of claim 5, further comprising fusing the tapered distal portion of the energy director to a bottom portion of the groove.

* * * * *